United States Patent [19]

Bengtsson et al.

[11] 4,289,781

[45] Sep. 15, 1981

[54] ANTI-PSYCHOTIC PHTHALIMIDINE DERIVATIVES

[75] Inventors: Karl S. Bengtsson; Seth O. Thorberg, both of Järna; Sven O. Ogren, Nykvarn, all of Sweden

[73] Assignee: Astra Läkemedel Aktiebolag, Södertälje, Sweden

[21] Appl. No.: 177,888

[22] Filed: Aug. 14, 1980

[30] Foreign Application Priority Data

Aug. 27, 1979 [SE] Sweden .................. 7907121

[51] Int. Cl.³ .................. C07D 401/04; A61K 31/40
[52] U.S. Cl. .................. 424/267; 546/200
[58] Field of Search .................. 546/200; 424/267

[56] References Cited

U.S. PATENT DOCUMENTS 4,053,615 10/1977 Boyle et al. .................. 546/200

FOREIGN PATENT DOCUMENTS 333734 3/1971 Sweden .
1271054 4/1972 United Kingdom .
1486104 1/1976 United Kingdom .
1425578 2/1976 United Kingdom .

Primary Examiner—John M. Ford
Attorney, Agent, or Firm—Brumbaugh, Graves, Donohue & Raymond

[57] ABSTRACT

Compounds having antipsychotic activity, characterized by the formula

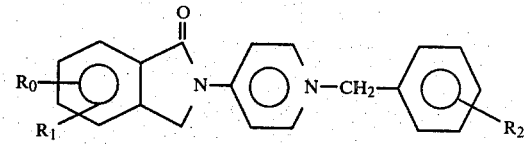

in which formula $R_o$ and $R_1$ are the same or different and are each selected from hydrogen, halogen, alkyl having 1, 2 or 3 carbon atoms, alkoxy having 1, 2 or 3 carbon atoms, and trifluoromethyl, and $R_2$ is selected from hydrogen, halogen, alkyl having 1, 2 or 3 carbon atoms, alkoxy having 1, 2 or 3 carbon atoms, and trifluoromethyl, pharmaceutical compositions containing them, and a method for the treatment of psychoses.

13 Claims, No Drawings

ANTI-PSYCHOTIC PHTHALIMIDINE DERIVATIVES

DESCRIPTION

1. Technical Field

The present invention relates to novel, pharmacologically active compounds, methods for their preparation and their therapeutical use. The invention also relates to pharmaceutical compositions containing the compounds. More particularly, the novel compounds of the invention are neuropharmacologically active compounds intended for the treatment of psychotic disorders, such as schizophrenia and mania.

The object of the present invention is to provide phthalimidine derivatives which have improved antipsychotic or neuroleptic effects.

2. Background Art

Sulpiride, (U.S. Pat. No. 3,342,826) with the formula

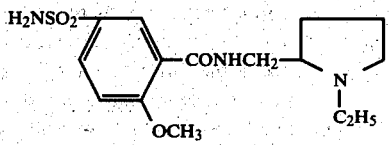

is a recently marketed antipsychotic agent. Sulpiride produces weak extrapyramidal side effects in humans and weak catalepsy in experimental animals, but has to be given in large dosages to obtain the desired effect.

DISCLOSURE OF THE INVENTION

Although sulpiride has valuable properties we have found compounds which are still better. These new antipsychotic compounds are characterized by the general formula

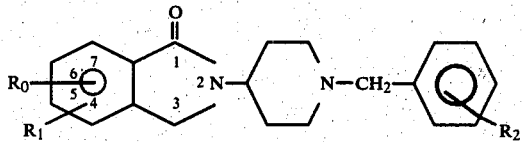

wherein $R_0$ and $R_1$, which may each be placed in any of the positions 4, 5, 6 or 7, are the same or different and are each selected from hydrogen, halogen, alkyl having 1, 2 or 3 carbon atoms, alkoxy having 1, 2 or 3 carbon atoms, and trifluoromethyl, and $R_2$ is selected from hydrogen, halogen, alkyl having 1, 2 or 3 carbon atoms, alkoxy having 1, 2 or 3 carbon atoms, and trifluoromethyl.

Pharmaceutically acceptable acid-addition salts of the compounds of the formula I are also comprised by this invention.

Preferred subgroup of compounds within the invention are obtained when (I) the groups $R_0$ and $R_1$, are the same or different and are each selected from hydrogen, halogen, alkyl having 1, 2 or 3 carbon atoms, alkoxy having 1, 2 or 3 carbon atoms, and trifluoromethyl, and $R_2$ is selected from hydrogen, halogen, methyl, trifluoromethyl, and alkoxy having 1, 2 or 3 carbon atoms; or (II) the groups $R_0$ and $R_1$ are the same or different and are each selected from hydrogen, halogen, methyl, trifluoromethyl, and methoxy, and $R_2$ is selected from hydrogen, halogen, methyl, trifluoromethyl, and methoxy; or (III) the groups $R_0$ and $R_1$ are the same or different and are each selected from hydrogen, halogen, and methoxy, and $R_2$ is selected from hydrogen, halogen, methyl, trifluoromethyl and alkoxy having 1, 2 or 3 carbon atoms; or (IV) the group $R_0$ is selected from hydrogen, halogen, and methoxy, $R_1$ is hydrogen, and $R_2$ is selected from hydrogen, halogen, methyl, trifluoromethyl, and alkoxy having 1, 2 or 3 carbon atoms; or (V) the group $R_0$ is in 5-position and is selected from hydrogen, halogen, alkyl having 1, 2 or 3 carbon atoms, alkoxy having 1, 2 or 3 carbon atoms, and trifluoromethyl, $R_1$ is hydrogen, and $R_2$ is selected from hydrogen, halogen, methyl, trifluoromethyl, and alkoxy having 1, 2 or 3 carbon atoms; or (VI) the group $R_0$ is in 5-position and is selected from hydrogen, fluorine, chlorine, bromine, methyl, and trifluoromethyl, $R_1$ is hydrogen, and $R_2$ is selected from hydrogen, chlorine, bromine, methyl, trifluoromethyl, and methoxy; or (VII) the group $R_0$ is in 5-position and is selected from hydrogen, fluorine, chlorine, bromine, and methyl, $R_1$ is hydrogen, and $R_2$ is selected from chlorine, methyl and methoxy.

It is especially preferred that the group $R_2$ is placed in para-position in the benzene ring. It is also preferred that the group $R_0$ is in 5-position in the benzene ring.

Especially preferred subgroups of compounds within the invention are obtained when (VIII) the group $R_0$ is in 5-position and is selected from halogen, alkyl having 1, 2 or 3 carbon atoms, alkoxy having 1, 2 or 3 carbon atoms, and trifluoromethyl, $R_1$ is hydrogen, and $R_2$ is selected from hydrogen, halogen, methyl, trifluoromethyl, and methoxy; or (IX) the group $R_0$ is in 5-position and is selected from fluorine, chlorine, bromine, methyl, methoxy, and trifluoromethyl, $R_1$ is hydrogen, and $R_2$ is selected from halogen, methyl, trifluoromethyl, and methoxy; or (X) the group $R_0$ is in 5-position and is selected from fluorine, chlorine, bromine, methyl, methoxy and trifluoromethyl, $R_1$ is hydrogen, and $R_2$ is in 4-position and is selected from halogen, methyl, trifluoromethyl, and methoxy.

Illustrative examples of compounds included in the invention are given in the following table, wherein the meanings of $R_0$, $R_1$ and $R_2$ refer to the formula I above.

| $R_0$ | $R_1$ | $R_2$ |
|---|---|---|
| 5-F | H | H |
| 6-F | H | H |
| 5-Br | H | H |
| 5-Cl | H | H |
| 6-Cl | H | H |
| 4-OCH$_3$ | 7-OCH$_3$ | H |
| 4-Br | 7-Br | H |
| 5-Cl | H | 4-OCH$_3$ |
| 4-F | H | H |
| 7-F | H | H |
| 5-CH$_3$ | H | 4-CH$_3$ |
| 5-Br | H | 4-Cl |
| H | H | H |
| 5-Br | H | 4-CH$_3$ |
| 5-Cl | H | 4-Cl |
| 5-CL | H | 4-CH$_3$ |
| 5-Cl | H | 3-CF$_3$ |
| 4-Br | 7-OCH$_3$ | 4-CH$_3$ |
| 5-Cl | 7-OCH$_3$ | 4-CH$_3$ |

-continued

| R₀ | R₁ | R₂ |
|---|---|---|
| 4-Br | 7-OCH₃ | 4-Cl |
| 4-Cl | 7-OCH₃ | 4-CH₃ |
| 5-CF₃ | H | 4-CH₃ |
| 5-CF₃ | H | 4-Cl |
| 5-Cl | H | 4-CF₃ |
| 5-OCH₃ | H | 4-Cl |
| 5-i-propyl | H | 4-Cl |
| 5-i-propoxy | H | 4-Cl |
| 5-Cl | 4-Cl | 4-Cl |
| 5-Cl | H | 4-C₂H₅ |
| 5-Cl | H | 4-i-propyl |
| 5-C₂H₅ | H | 4-CH₃ |
| 5-OC₂H₅ | H | 4-Cl |
| 5-Br | 7-OCH₃ | 4-CH₃ |
| 5-CH₃ | 4-Br | 4-CH₃ |
| 5-CH₃ | 7-OCH₃ | 4-CH₃ |
| 5-Br | H | 4-OCH₃ |

The compounds of this invention may be administered in the form of free bases or their salts with non-toxic acids. Some typical examples of these salts are hydrobromide, hydrochloride, phosphate, sulphate, citrate and tartrate.

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrochloride, hydrobromide, lactate, acetate, sulphate, tartrate and the like in association with a pharmaceutically acceptable carrier. Accordingly, terms relating to the novel compounds of this invention whether generically or specifically are intended to include both free amine base and the acid addition salts of the free base, unless the context in which such terms are used, e.g. in the specific examples would be inconsistent with the broad concept. The carrier may be a solid, semi-solid or liquid diluent or capsule. These pharmaceutical preparations constitute a further aspect of this invention. Usually the active substance will constitute between 0.1 and 99% by weight of the preparation, preferably between 0.5 and 20% by weight for preparation intended for injection and between 2 and 95% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine and a lubricant such as magnesium stearate, calcium stearate, polyethylene glycol waxes, and the like, and then compressed to form tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl shaped closed capsules) consisting of gelatine and, for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules. Suitable peroral daily doses of the compounds of the invention are 100–500 mg, preferably 200–300 mg.

The compounds of the formula I of this invention can be prepared by any of the six hereinbelow described methods.

(A) The first method comprises reducing a compound of the formula

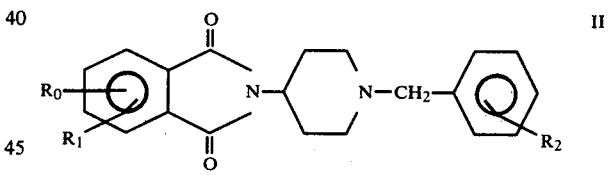

wherein $R_0$, $R_1$ and $R_2$ are defined as above, to the formation of a compound of the formula I. The reduction is preferably carried out by hydrogenating a liquid solution of this compound with Sn/HCl at elevated temperature.

The intermediate of the formula II wherein $R_2$ is not hydrogen is a novel compound constituting a further aspect of the invention, and can be prepared by known methods such as for example by reacting a compound of the formula

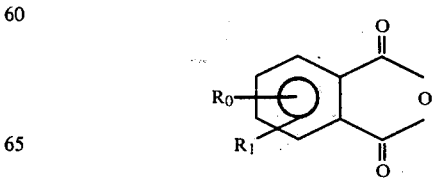

with a compound of the formula

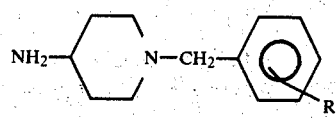

This reaction is preferably conducted by prolonged heating of a mixture of the reactants dissolved in an inert organic solvent.

(B) In a further method, the compound of the formula I of the invention can be prepared by reacting an ester of the formula

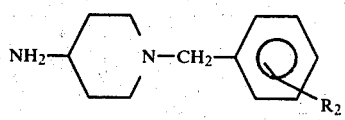

wherein $R_0$ and $R_1$ are defined as above, $R_3$ is an alkyl, aryl, or aralkyl group, and Hal is chlorine or bromine, with a compound of the formula

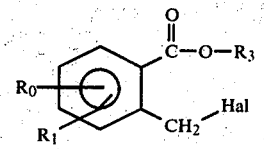

wherein $R_2$ is defined as above, to the formation of a compound of the formula I.

The reaction is preferably conducted in an inert organic solvent at elevated temperature.

The intermediate of the formula III can be prepared by known methods, such as for example by reacting a compound of the formula

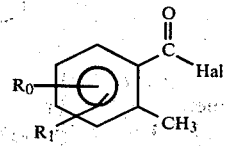

with bromine or chlorine, and then reacting the compound of the formula

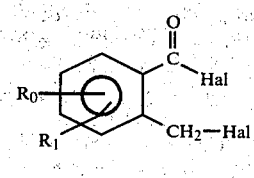

with an alcohol of the formula $R_3$—OH.

(C) In a further method, the compound of the formula I of the invention can be prepared by elimination of a carboxyl group from a compound of the formula

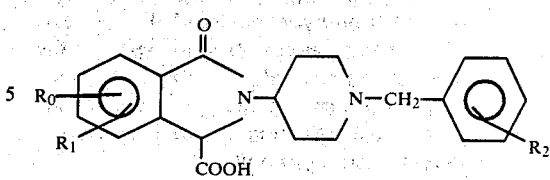

wherein $R_0$, $R_1$ and $R_2$ are defined as above, to the formation of a compound of the formula I. The elimination is preferably conducted by heating of the intermediate to about 100°–200° C. under dry conditions. The intermediate of the formula IV can be prepared by known methods, such as for example by reacting a compound of the formula

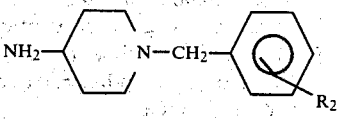

with a compound of the formula

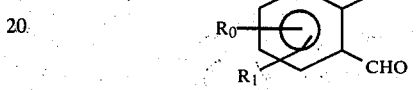

in the presence of a cyanide salt, to the formation of a nitrile of the formula

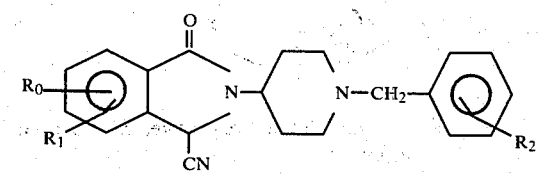

which is subsequently hydrolyzed to the carboxylic acid of the formula IV. (D) In a further method, the compound of the formula I of the invention can be prepared by reacting a compound of the formula

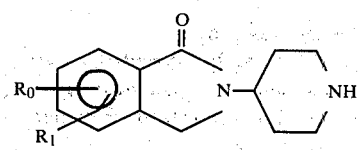

wherein $R_0$ and $R_1$ are defined as above, with a compound of the formula

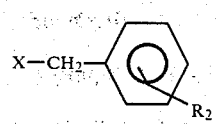

wherein $R_2$ is defined as above and X is chlorine, bromine, or p-toluenesulphonyloxy, to the formation of a compound of the formula I.

The reaction is preferably conducted in an inert organic solvent at elevated temperature.

The compounds of the formula V wherein both $R_0$ and $R_1$ are different from hydrogen, are believed to be novel compounds and constitute a further aspect of the invention. They can be prepared according to methods known per se. (E) In a further method, the compounds of the formula I of the invention can be prepared by reacting a compound of the formula

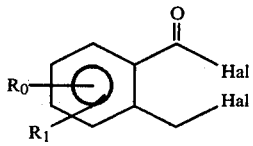   VI wherein $R_0$ and $R_1$ are defined as above and Hal is bromine or chlorine, with a compound of the formula

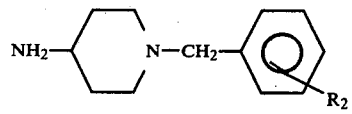

wherein $R_2$ is defined as above. The reaction is preferably carried out in an inert organic solvent at elevated temperature. (F) In a further method, the compounds of the formula I of the invention can be prepared by reacting a compound of the formula

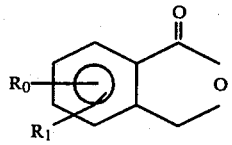   VII wherein $R_0$ and $R_1$ are defined as above, with a compound of the formula

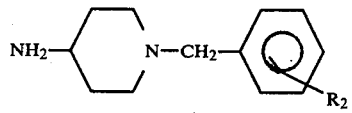

wherein $R_2$ is defined as above.

The reaction is preferably carried out by heating a mixture of the reactants in an inert solvent to superatmospheric pressure in a pressurized container.

BEST MODE OF CARRYING OUT THE INVENTION

The pharmacologically most satisfactory results have been obtained when using one of the compounds
5-chloro-2-[4-N-(4-methylbenzyl)-piperidyl]-phthalimidine,
5-bromo-2-[4-N-(4-methylbenzyl)-piperidyl]-phthalimidine,
5-chloro-2-[4-N-(4-methoxybenzyl)-piperidyl]-phthalimidine,
5-bromo-2-[4-N-(4-chlorobenzyl)-piperidyl]-phthalimidine, and
5-chloro-2-[4-N-(4-chlorobenzyl)-piperidyl]-phthalimidine.

WORKING EXAMPLES

EXAMPLE 1

Preparation of 2-(4-N-benzylpiperidyl)-5-fluorophthalimidine

Schematic illustration of the synthesis used (method A):

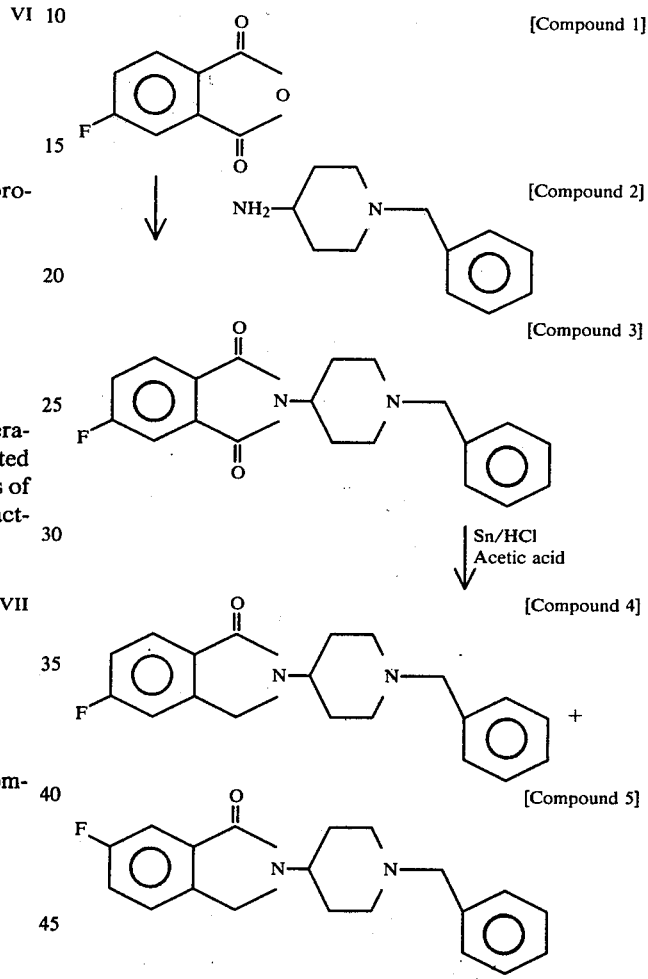

4-Fluoro-phthalic anhydride (1) was prepared according to known methods (G Valkanas and H Hopff, J. Chem. Soc. 1963 3475) 4-Amino-benzylpiperidine was synthetized according to Harper & Chighell (J. Med. Chem. 1964,7 (6) 729).

The above anhydride (1) (8.0 g, 0.050 mole) was dissolved in toluene (500 ml) and warmed to 50° C. 4-Amino-1-benzylpiperidine (2) (9.5 g, 0.050 mole) was dissolved in toluene (100 ml) and added dropwise in 15 minutes. The mixture was heated to reflux for 16 hours whereupon the solvent was evaporated in vacuum. The crystalline residue was dehydratized by heating to 200° C. After cooling, the product was dissolved in chloroform and recrystallized from chloroform-isopropanol. Yield 13.6 g (80%) M.p. 113°–114° C.

The phthalimide (3) (13.5 g, 0.040 mole) was dissolved in acetic acid (100 ml). Tin (11.2 g, 0.094 mole) was added and the mixture was cooled on ice. Concentrated hydrochloric acid (22 ml) was added dropwise and the mixture was heated to 120° C. for 16 hours. The clear solution was evaporated to nearly dryness and the residue was dissolved in dilute hydrochloric acid (100 ml, 1.0-N). The product was extracted as an ion-pair with dichloromethane (100 ml). The organic layer was washed with brine and made alkaline with sodium hydroxide (2-N). The organic phase was washed with water, dried over anhydrous sodium sulphate and evaporated in vacuum.

The residual oil contains a 80/20 mixture of the desired compound and its 6-fluoro isomer. The isomers were separated on a preparative HPLC 500 silica gel column with hexane (90)-ethanol (10)-conc. ammonia (0.2). as liquid phase. The yield of 2-(4-N-benzyl-piperidyl)-5-fluorophthalimidine (4) was 4.2 g (33%). M.p. 128°–129° C.

The yield of the isomer 2-(4-N-benzylpiperidyl)-6-fluoro phthalimidine (5), which was isolated from the same reaction-mixture, was 0.7 g (5%). M.p. 136°–138° C.

EXAMPLE 2

Preparation of 2-(4-N-benzylpiperidyl)-5-bromo phthalimidine

This compound (M.p. 173°–174° C., 30% yield) was prepared in analogy with Example 1 via 2-(4-N-benzyl-piperidyl) 5-bromo phthalimide (131°–133° C., 42% yield) from 4-bromophtalic anhydride. The starting material was prepared according to known method (JACS 51 (865–75) 1929).

EXAMPLE 3

Preparation of 2-(4-N-benzylpiperidyl)-5-chloro phthalimidine and 2-(4-N-benzylpiperidyl)-6-chloro phthalimidine.

The 5-chloro-compound (M.p. 151°–152° C., 20% yield) and its 6-chloro-isomer (M.p. 125°–126° C., 5% yield) were prepared in analogy with Example 1 via 2-(4-N-benzylpiperidyl) -5-chloro phthalimide (M.p. 126°–127° C., 83% yield) from 4-chloro phthalic anhydride. loc. cit.

EXAMPLE 4

Preparation of 2-(4-N-benzylpiperidyl)-4,7-dimethoxy-phthalimidine

This compound (M.p. 175°–177° C., Yield 22%) was prepared in analogy with Example 1 via 2-(4-N-benzyl-piperidyl)-4,7-dimethoxy phthalimide (M.p. 159°–160° C., 80% yield) from 3,6-dimethoxy phthalic anhydride. The anhydride was prepared according to known methods (G D Graves and R Adams, JACS 45 2447,1923).

EXAMPLE 5

Preparation of 2-(4-N-benzylpiperidyl)-5,6-dibromo phthalimidine

This compound (M.p. 176°–180° C., 69% yield) was prepared in analogy with Example 1 via 2-(4-N-benzyl-piperidyl)-5,6-dibromo phthalimide (M.p. 177°–78° C., yield 65%) from 4,5-dibromophthalic anhydride. The anhydride was prepared according to known methods (Frame and Wilson, Journal of Organic Chemistry, 732–49, 1941).

EXAMPLE 6

Preparation of 2-(4-N-benzylpiperidyl) -4,7-dibromo phthalimidine.

This compound (M.p. 143°–145° C., 51% yield) was prepared in analogy with Example 1 via 2-(4-N-benzyl-piperidyl)-4,7-dibromo phthalimide (M.p. 194°–195° C., 66% yield) from 3,6-dibromo phthalic anhydride. loc. cit.

EXAMPLE 7

Preparation of 5-chloro-2-[4-N-(4-methoxybenzyl)piperidyl]-phthalimidine

This compound (M.p. 135°–137° C.; yield 20%) was prepared in analogy with Example 1 via 2-[4-N-(4-methoxybenzyl)piperidyl]-5-chloro-phthalimide (M.p. 131°–134° C.; yield 50%), obtained from 4-chlorophthalic anhydride and 4-amino-N-(4-methoxybenzyl)-piperidine.

EXAMPLE 8

Preparation of 2-(4-N-benzylpiperidyl)-4-fluoro-phthalimidine hydrochloride.

This compound (M.p. 290°–295° C., decomposition; yield 20%) was prepared in analogy with Example 1 via 2-(4-N-benzylpiperidyl)-4-fluoro-phthalimide (M.p. 136°–137° C.; yield 76%), obtained from 3-fluorophthalic anhydride and 4-amino-N-benzylpiperidine.

EXAMPLE 9

Preparation of 7-fluoro-2-[4-N-benzyl piperidyl]phthalimidine

This compound (M.p. 126°–127° C.; yield 8%) was obtained as a by-product at the synthesis in Example 8.

EXAMPLE 10

Preparation of 5-methyl-2-[4-N-(4-methylbenzyl)piperidyl]-phthalimidine hydrochloride This compound (M.p. 290°–293° C.; yield 31%) was prepared in analogy with Example 1 via 5-methyl-2-[4-N-(4-methylbenzyl)-piperidyl]-phthalimide (M.p. 153°–155° C., yield 75%) from 4-methylphthalic anhydride and 4-amino-N-(4-methylbenzyl)piperidine.

EXAMPLE 11

Preparation of 5-bromo-2-[4-N-(4-chlorobenzyl)-piperidyl]-phthalimidine

Schematic illustration of the synthesis used (method B):

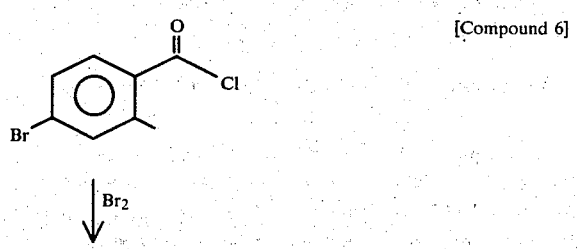

[Compound 6]

-continued

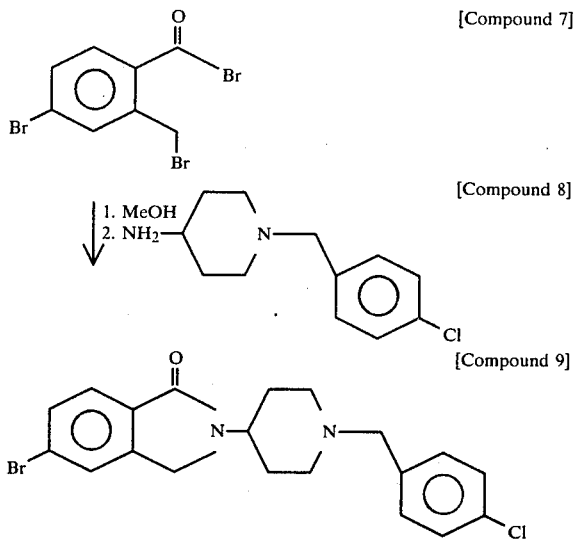

4-Bromo-2-methyl-benzoyl chloride (6) J. O. Harris, J Chem Soc 1947, 690), was brominated with 1.1 equ. of bromine in analogy with a known method [W. Davies and W. H. Perkin, J Chem Soc 121, 2202 (1922] giving 66% of 4-bromo-2-bromomethyl-benzoyl bromide (7) after distillation. B.p. 99°–102° C. at 5 Pa.

The above bromide (3.57 g, 10 mmol) was esterified with 0.80 ml (20 mmol) of methanol in 15 ml of methylene chloride giving the crude methyl 4-bromo-2-bromomethyl benzoate in a quantitative yield.

4-Amino-N-(4-chlorobenzyl)piperidine (8) (B.p. 112° C. at 33 Pa) was prepared from N-4-chlorobenzyl-4-piperidon. (See Method A). 2.25 g (10 mmol) of the amine (8) was heated in 50 ml of toluene to 105°–110° C. and 10 mmol of the crude methyl 4-bromo-2-bromomethyl-benzoate dissolved in 15 ml of toluene was added during 15 minutes. After another 15 minutes at 110° C. the solution was cooled, washed with a weak sodium hydroxide solution and water, dried and evaporated. The residue was recrystallized from 2-propanol giving 1.80 g (43%) of 5-bromo-2-[4-N-(4-chlorobenzyl)piperidyl]phthalimidine. A second recrystallization gives 1.38 g, m.p. 190.5°–192° C.

EXAMPLE 12

Preparation of 2-(4-N-benzyl-piperidyl)phthalimidine

This compound (M.p. 136°–138° C., yield 66%) was prepared in analogy with Example 11 from 2-bromomethyl-benzoyl bromide [Synthesized by W. Davies and W. H. Perkin, J Chem Soc 121, 2202 (1922)] and 4-amino-N-benzyl piperidine (see method A).

EXAMPLE 13

Preparation of 2-(4-N-benzyl-piperidyl)-6-bromo phthalimidine

This compound (M.p. 139°–141° C., yield 32%) was prepared in analogy with Example 11 from 5-bromo-2-bromomethyl-benzoyl bromide (B.p. 102°–104° C. at 4.0 Pa) and 4-amino-N-benzyl piperidine (see method A).

EXAMPLE 14

Preparation of 5-bromo-2-[4-N-(4-methylbenzyl-piperidyl]phthalimidine

This compound (M.p. 168.5°–170.0° C., yield 45%) was prepared in analogy with Example 11 from 4-bromo-2-bromomethyl-benzoyl bromide and 4-amino-N-(4-methylbenzyl)piperidine (B.p. 108°–110° C. at 9 Pa).

EXAMPLE 15

Preparation of 5-chloro-2-[4-N-(4-chlorobenzyl)piperidyl)-phthalimidine

This compound (M.p. 172°–174° C.; yield 21%) was prepared in analogy with Example 11 from 4-chloro-2-bromomethylbenzoyl bromide (B.p. 84°–86° C. at 0.7 Pa) and 4-amino-N-(4-chlorobenzyl)piperidine. The latter intermediate was prepared by reductive amination of the corresponding substituted 1-benzyl-4-piperidon according to known methods (G. M. Rosen; J. Med. Chem. 1974 vol. 17,3, p 359).

EXAMPLE 16

Preparation of 5-chloro-2-[4-N-(4-methylbenzyl)piperidyl]-phthalimidine

This compound (M.p. 153°–154.5° C.; yield 41%) was prepared in analogy with Example 11 from 4-chloro-2-bromomethylbenzoyl bromide (B.p. 84°–86° C., 0.7 Pa) and 4-amino-N-(4-methylbenzyl)piperidine.

EXAMPLE 17

Preparation of 2-(4-N-benzylpiperidyl)-6,7-dimethoxy phthalimidine hydrochloride Schematic illustration of the synthesis used (method C):

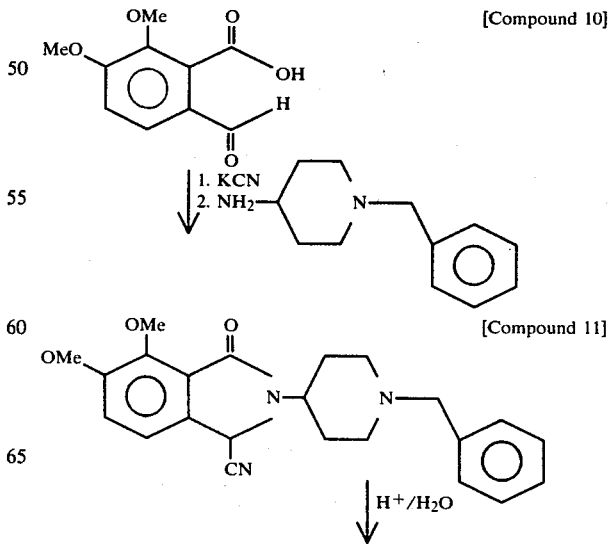

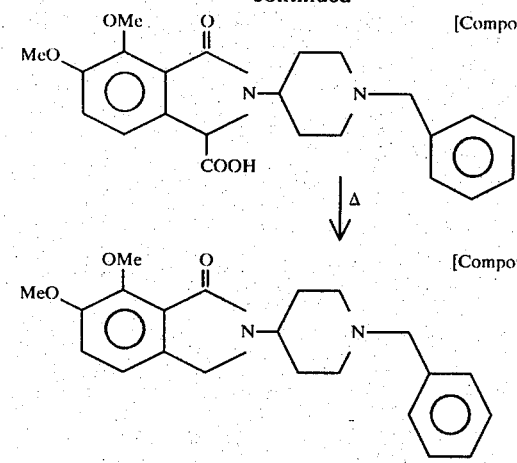

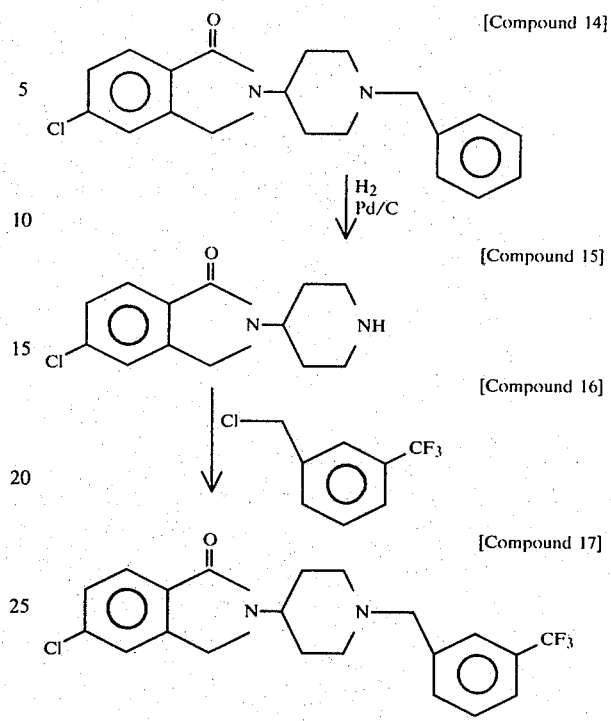

Opianic acid (10) was prepared according to known method (Wilson, Zirkte and Anderson, J Org. Chem. 16 (792-8) 1951.

In an ice-cooled suspension of opianic acid (8.7 g, 0.041 mole) in water (45 ml), potassiumcyanide (3.5 g, 0.054 mole) was added in portions. A clear solution was formed. The solution was stirred for one and a half hour. 4-Amino-1-benzyl-piperidine (8.7 g, 0.045 mole) was dissolved in methanol (45 ml) and added dropwise at 0°–3° C. in 10 minutes. Stirring was continued for 1 hour on ice-bath. The mixture was acidified to pH 2.0 and heated to reflux for 20 minutes. After cooling the mixture was evaporated in vacuum. The product 2-(4-N-benzylpiperidyl)-3-cyano-6,7-dimethoxy phthalimidine was recrystallized from ethanol. Yield 8.7 g (54%) M.p. 226°–228° C.

The cyano derivate (11) (7.5 g, 0.019 mole) was mixed with sodium hydroxide 2-N (67 ml) and ethanol (45 ml) and the mixture was heated to reflux for 12 hours. The solvent was evaporated in vacuum. The residual aqueous solution was washed twice with ether and acidified with concentrated hydrochloric acid to pH 1. A light brown oily precipitate was obtained. The product was collected by decantation and dried in vacuum over night. The yield of 2-(4-N-benzylpiperidyl)-3-carboxy-6,7-dimethoxy phthalimidine (12) was 5.0 g (64%). M.p. 115°–120° C. dec.

The carboxylic acid derivate (12) (4.5 g, 0.01 mole) was heated under dry conditions with stirring to 150° C., and stirred for ½ hour. The desired 6,7-dimethoxy-2-(4-N-benzylpiperidyl)phthalimidine hydrochloride was cooled and recrystallized from ethanol. Yield 2.15 g (59%). M.p. 267°–269° C.

EXAMPLE 18

Preparation of 5-chloro-2-[4-N-(3-trifluoromethylbenzyl)-piperidyl]-phthalimidine Schematic illustration of the synthesis used (method D):

The intermediate 2-(4-piperidyl)-5-chloro-phthalimidine (15) was prepared by removing the benzyl group from 2-(4-N-benzylpiperidyl)-5-chloro-phthalimidine (14) by catalytic hydrogenation. The hydrogenation was effected by dissolving the compound (14) (8 g, 0.0212 mol, hydrochloride salt) in 50% ethanol/H₂O-solution. The catalyst (5% Pd/C) was added and then an equivalent amount of hydrogen was added during 65 minutes at normal pressure and at a temperature of 58° C. The catalyst was filtered off and the filtrate was evaporated to dryness in vacuum. The crystalline residue was made acidic with hydrogen chloride and the hydrochloride salt was recrystallized from ethanol. M.p. 312°–314° C., yield 97%.

The obtained intermediate 2-(4-piperidyl)-5-chloro-phthalimidine (15) (1.17 g, 0.00467 mol) was dissolved in 30 ml benzene. Potassium carbonate (1.93 g, 0.0140 mole) and potassium iodide (0.78 g, 0.00607 mole) was added whereupon 3-trifluoromethylbenzylchloride (1.18 g, 0.00607 mole) dissolved in benzene was added drop-wise at room temperature, and was then heated under reflux during three days. The inorganic salts were filtered off and the filtrate was evaporated to dryness in vacuum. The residue was re-crystallized with cyclohexane isopropylether (M.p. 115°–117° C., yield 63%).

EXAMPLE 19

Preparation of 2-(4-N-benzylpiperidyl)-5-bromophthalimidine

Schematic illustration of the synthesis used (method E):

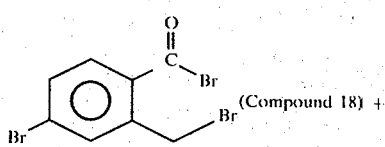

-continued

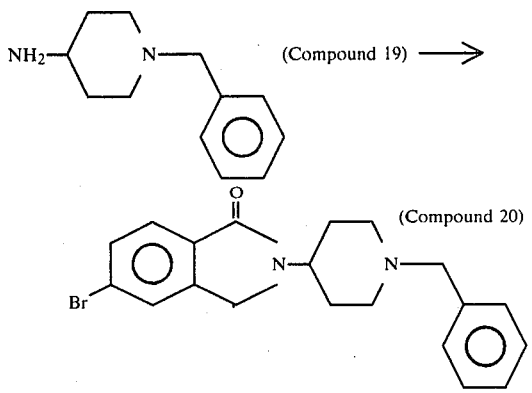

4-Amino-1-benzylpiperidine (0.76 g, 4 mmole) was added to 4-bromo-2-bromomethyl-benzoylbromide (0.72 g, 2 mmole) dissolved in toluene, and the mixture was heated to reflux for four hours. Working-up of the reaction mixture and separation on silica gel yielded 0.12 g (17%) of a product which showed to be identical with the product in Example 2 according to thin-layer chromatography and mass-spectrography.

EXAMPLE 20

Preparation of 2-(4-N-benzylpiperidyl)phthalimidine

Schematic illustration of the synthesis used (method F):

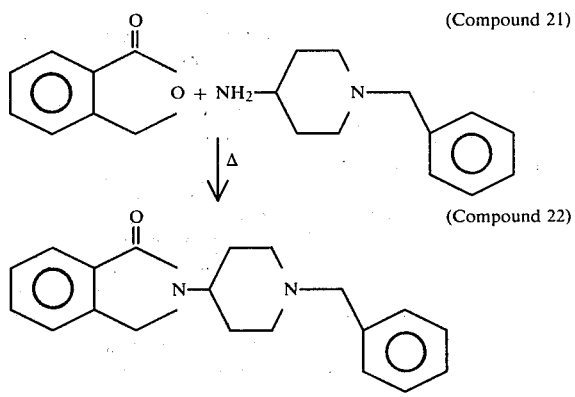

1-Benzyl-4-aminopiperidine (1.90 g, 0.01 mol) was dissolved in 20 ml methanol/H$_2$O (70%). Phthalide (1.34 g, 0.01 mol) was added whereupon the mixture was heated in a pressurized container during 15 hours at 160° C. The reaction mixture was evaporated to dryness in vacuum, the residue was dissolved in diluted HCl/aq., and was washed with ethyl ether. The water phase was made alkaline, and was then washed and dried. The etheral solution was evaporated in vacuum. The residue (1.8 g) was analysed with thin-layer chromatography and high-performance liquid chromatography, and was found to contain the starting amine and 34% of the desired product, which was shown to be identical with the product in Example 12.

Pharmaceutical Preparations

The following examples illustrate how the compounds of the present invention may be included in pharmaceutical preparations.

EXAMPLE I

Preparation of soft gelatin capsules 500 g of active substance were mixed with 500 g of corn oil, whereupon the mixture was filled in soft gelatin capsules, each capsule containing 100 mg of the mixture (i.e. 50 mg of active substanse).

EXAMPLE II

Preparation of soft gelatin capsules 500 g of active substance were mixed with 750 g of peanut oil, whereupon the mixture was filled in soft gelatin capsules, each capsule containing 125 mg of the mixture (i.e. 50 mg of active substance).

EXAMPLE III

Preparation of tablets 50 kg of active substance were mixed with 20 kg of silicic acid of the trade mark Aerosil. 45 kg of potato starch and 50 kg of lactose were mixed therewith and the mixture was moistened with a starch paste prepared from 5 kg of potato starch and destilled water, whereupon the mixture was granulated through a sieve. The granulate was dried and sieved, whereupon 2 kg of magnesium stearate was mixed into it. Finally the mixture was pressed into tablets each weighing 172 mg.

EXAMPLE IV

Preparation of effervescing tablets 100 g of active substance, 140 g of finely divided citric acid, 100 g of finely divided sodium hydrogen carbonate, 3.5 g of magnesium stearate and flavouring agents were mixed and the mixture was pressed into tablets each containing 100 mg of active substance.

EXAMPLE V

Preparation of a sustained release tablet 200 g of active substance were melted with 50 g of stearic acid and 50 g of carnauba wax. The mixture thus obtained was cooled and ground to a particle size of less than 1 mm in diameter. The mixture thus obtained was mixed with 5 g of magnesium stearate and pressed into tablets each weighing 305 mg. Each tablet thus contains 200 mg of active substance.

Pharmacology

Introduction

An abundance of studies suggest that the antipsychotic action of neuroleptics is in some way related to the decrease in catecholamine transmission in the brain caused by these drugs and more specifically due to central dopamine (DA) receptor blockade as originally suggested by Carlsson (Acta Pharmacol. 20, 140–144, 1963; J Neur. Transmission, 34, 125–132, 1973).

Most compounds with an antipsychotic action appear to affect several DA systems in the brain. It has been hypothetized that the antipsychotic action may be linked to blockade of DA receptors in the subcortical and cortical limbic structures (J Pharm. Pharmacol. 25, 346, 1973; Lancet, Nov. 6, 1027, 1976) or to blockade of DA receptors in the nigroneostriatal DA system (Intern. J. Neurol. 6, 27–45, 1967).

There are several techniques available to study DA receptor blockade in the brain. One method is based on the ability of anti-psychotics to block the behavioural effects induced by the DA agonist apomorphine. Apomorphine produces a characteristic syndrome in rats and other species consisting of repetitive movements (stereotypies) and hyperactivity which appear to be due to activation of postsynaptic DA receptors in the brain (J Pharm. Pharmacol. 19, 627, 1967; J Neurol. Transm. 40, 97–113, 1977). The stereotypies (chewing, licking, biting) appear mainly to reflect action on DA receptors of the neostriatal system (J Phychiat. Res., 11, 1, 1974) whereas the increased locomotion (hyperactivity) mainly appears to be due to activation of DA receptors in mesolimbic structures (nucleus olfactorium, nucleus accumbens), (J Pharm. Pharmacol. 25, 1003, 1973).

A number of studies have demonstrated that neuroleptics block apomorphine stereotypies and that this blockade is well related to blockade of DA transmission measured by other techniques. Thus, the antiapomorphine effect correlates with changes in DA turnover (Eur. J. Pharmacol., 11, 303, 1970), DA receptor binding studies (Life Science, 17, 993–1002, 1976) and most important with antipsychotic efficacy (Nature, 263, 388–341, 1976).

Methods

Male Sprague-Dawley rats weighing 225–275 g were used. The rats were observed in perspex cages (40 (L)×25 (w)×30 (h) cm) and the behaviour was scored 5,20,40, and 60 min after the injection of apomorphine. The compounds were injected 60 min prior to apomorphine hydrochloride (1 mg/kg) which was injected subcutaneously into the neck. This dose and form of administration was found to produce a very consistent response and very low variation in response strength. Furthermore, apomorphine given s.c. also produced a very consistent hyperactivity.

Directly after injection, the animals were placed in the cages, one in each cage. Scoring of the stereotypies were performed by two separate methods. The first scoring system was a modified version of the system introduced by Costall and Naylor (1973). The strength of the stereotypy was scored on a 0–3 scale as follows:

| Score | Description of stereotyped behaviour. |
|---|---|
| 0 | No change in behaviour compared to saline controls. No sedation. |
| 1 | Discontinuous sniffing. |
| 2 | Continuous sniffing. |
| 3 | Continuous sniffing. Chewing, biting and licking. |

In the second system the number of animals displaying hyperactivity caused by apomorphine were scored. Each group consisted of 6–8 animals. Saline controls were always run simultaneously. $ED_{50}$'s are in the first scoring system (0–3 scale), the doses which reduce the strength of the stereotypies by 50% over the observation period of 60 min. $ED_{50}$'s of the second scoring system are the doses which reduce the number of animals showing hyperactivity by 50% over the observation period of 60 min. The $ED_{50}$'s were calculated from log dose-response curves by the method of least squares from 4–6 dose levels with 6–8 animals per dose level.

Results

Compounds of the invention were compared with the antipsychotic sulpiride (Life Science, 17, 1551–1556, 1975), using the test method described above. The results are presented in Table 1.

TABLE 1

| | The ability to block apomorphine induced stereotypies and hyperactivity | |
|---|---|---|
| Compound according to Example No. | Stereotypies $ED_{50}$ μmol/kg i.p. | Hyperactivity $ED_{50}$ μmol/kg i.p. |
| 1 ($R_o$ = 5-F; $R_1$ = H; $R_2$ = H) | 22.0 | 4.0 |
| 2 ($R_o$ = 5-Br; $R_1$ = H; $R_2$ = H) | 17.5 | 14 |
| 3 ($R_o$ = 5-Cl; $R_1$ = H; $R_2$ = H) | 16.0 | 2.0 |
| 7 ($R_o$ = 5-Cl; $R_1$ = H; $R_2$ = 4-OCH$_3$) | 9.5 | 2.2 |
| 11 ($R_o$ = 5-Br; $R_1$ = H; $R_2$ = 4-Cl) | 11 | 3.4 |
| 14 ($R_o$ = 5-Br; $R_1$ = H; $R_2$ = 4-CH$_3$) | 6.5 | 1.7 |
| 15 ($R_o$ = 5-Cl; $R_1$ = H; $R_2$ = 4-Cl) | 14 | 3.5 |
| 16 ($R_o$ = 5-Cl; $R_1$ = H; $R_2$ = 4-CH$_3$) | 9 | 0.9 |
| Sulpiride | 293 | 45 |

The tabulated results indicate that the compounds of the present invention are potent inhibitors of DA receptors in the brain. Due to their ability to antagonize both apomorphine stereotypies and hyperactivity they probably block DA receptors in both striatal and limbic area (see Introduction). Furthermore they are considerably more active than the antipsychotic drug sulpiride. Since there is a highly significant correlation between the blockade of apomorphine and clinical antipsychotic efficacy (Nature, 263, 388–341, 1976), it is very likely that the compounds of the present invention will show a highly potent antipsychotic action in man.

We claim:

1. A compound of the formula

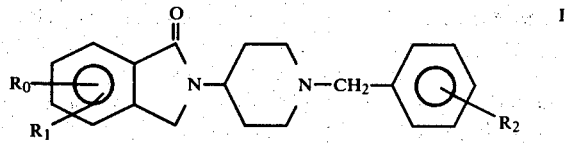

and pharmaceutically acceptable acid-addition salts thereof, in which formula $R_0$ and $R_1$ are the same or different and are each selected from hydrogen, halogen, alkyl having 1, 2 or 3 carbon atoms, alkoxy having 1, 2 or 3 carbon atoms, and trifluoromethyl, and $R_2$ is selected from hydrogen, halogen, alkyl having 1, 2 or 3 carbon atoms, alkoxy having 1, 2 or 3 carbon atoms, and trifluoromethyl.

2. A compound according to claim 1 wherein $R_0$ and $R_1$ in formula I are the same or different and are each selected from hydrogen, halogen, methyl and methoxy, and $R_2$ is selected from hydrogen, halogen, methyl, trifluoromethyl, and methoxy.

3. A compound according to claim 1 wherein $R_0$ in formula I is in 5-position and is selected from fluorine, chlorine, bromine, methyl, methoxy, and trifluoromethyl, $R_1$ is hydrogen, and $R_2$ is selected from halogen, methyl, trifluoromethyl, and methoxy.

4. A compound according to claim 1 selected from 5-chloro-2-[4-N-(4-methylbenzyl)-piperidyl]-phthalimidine, 5-bromo-2-[4-N-(4-methylbenzyl)-piperidyl]-phthalimidine, 5-chloro-2-[4-N-(4-methoxybenzyl)-piperidyl]-phthalimidine, 5-bromo-2-[4-N-(4-chlorobenzyl)-piperidyl]-phthalimidine, and 5-chloro-2-[4-N-(4-chlorobenzyl)-piperidyl]-phthalimidine.

5. A pharmaceutical preparation which comprises as active ingredient a therapeutically effective amount for the treatment of psychoses of a compound of the formula

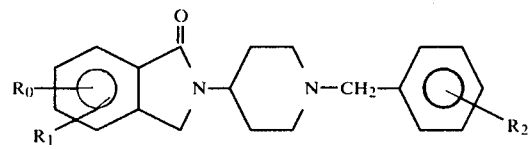

or a pharmaceutically acceptable acid-addition salt thereof, in which formula $R_0$ and $R_1$ are the same or different and are each selected from hydrogen, halogen, alkyl having 1, 2 or 3 carbon atoms, alkoxy having 1, 2 or 3 carbon atoms, and trifluoromethyl, and $R_2$ is selected from hydrogen, halogen, alkyl having 1, 2 or 3 carbon atoms, alkoxy having 1, 2 or 3 carbon atoms, and trifluoromethyl, in association with a pharmaceutically acceptable carrier.

6. A pharmaceutical preparation according to claim 5 in dosage unit form.

7. A pharmaceutical preparation according to claim 5, wherein the groups $R_0$ and $R_1$ in formula I are the same or different and are each selected from hydrogen, halogen, methyl and methoxy, and $R_2$ is selected from hydrogen, halogen, methyl, trifluoromethyl, and methoxy.

8. A pharmaceutical preparation according to claim 5, wherein $R_0$ in formula I is in 5-position and is selected from fluorine, chlorine, bromine, methyl, methoxy, and trifluoromethyl, $R_1$ is hydrogen, and $R_2$ is selected from halogen, methyl, trifluoromethyl, and methoxy.

9. A pharmaceutical preparation according to claim 5, wherein the compound of the formula I is selected from 5-chloro-2-[4-N-(4-methylbenzyl)-piperidyl]-phthalimidine, 5-bromo-2-[4-N-(4-methylbenzyl)-piperidyl]-phthalimidine, 5-chloro-2-[4-N-(4-methoxybenzyl)-piperidyl]-phthalimidine, 5-bromo-2-[4-N-(4-chlorobenzyl)-piperidyl]-phthalimidine, and 5-chloro-2-[4-N-(4-chlorobenzyl)-piperidyl]-phthalimidine.

10. A method for the treatment of psychoses in man, characterized by the administration to a host in need of such treatment of a therapeutically effect amount of a compound of the formula

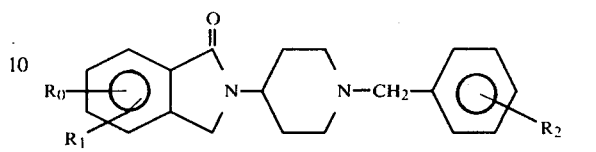

or a pharmaceutically acceptable acid-addition salt thereof, in which formula $R_0$ and $R_1$ are the same or different and are each selected from hydrogen, halogen, alkyl having 1, 2 or 3 carbon atoms, alkoxy having 1, 2 or 3 carbon atoms, and tridluoromethyl, and $R_2$ is selected from hydrogen, halogen, alkyl having 1, 2 or 3 carbon atoms, alkoxy having 1, 2 or 3 carbon atoms, and trifluoromethyl.

11. A method according to claim 10 wherein the groups $R_0$ and $R_1$ in formula I are the same or different and are each selected from hydrogen, halogen, methyl and methoxy, and $R_2$ is selected from hydrogen, halogen, methyl, trifluoromethyl, and methoxy.

12. A method according to claim 10 wherein $R_0$ in formula I is in 5-position and is selected from fluorine, chlorine, bromine, methyl, methoxy, and trifluoromethyl, $R_1$ is hydrogen and $R_2$ is selected from halogen, methyl, trifluoromethyl, and methoxy.

13. A method according to claim 10 wherein the compound of the formula I is selected from 5-chloro-2-[4-N-(4-methylbenzyl)-piperidyl]-phthalimidine, 5-bromo-2-[4-N-(4-methylbenzyl)-piperidyl]-phthalimidine, 5-chloro-2-[4-N-(4-methoxybenzyl)-piperidyl]-phthalimidine, 5-bromo-2-[4-chlorobenzyl)-piperidyl]-phthalimidine, and 5-chloro-2-[4-N-(4-chlorobenzyl)-piperidyl]-phthalimidine.

* * * * *